United States Patent
Yadav et al.

(10) Patent No.: US 6,726,992 B1
(45) Date of Patent: Apr. 27, 2004

(54) NANO-ENGINEERED PHOSPHORS AND RELATED NANOTECHNOLOGY

(75) Inventors: Tapesh Yadav, Longmont, CO (US); Karl Pfaffenbach, Boulder, CO (US)

(73) Assignee: NanoProducts Corporation, Longmont, CO (US)

( * ) Notice: Subject to any disclaimer, the term of this patent is extended or adjusted under 35 U.S.C. 154(b) by 0 days.

(21) Appl. No.: 10/464,208

(22) Filed: Jun. 18, 2003

Related U.S. Application Data

(62) Division of application No. 10/004,387, filed on Dec. 4, 2001, and a division of application No. 10/150,722, filed on May 17, 2002, and a division of application No. 09/274,517, filed on Mar. 23, 1999, now Pat. No. 6,344,271.
(60) Provisional application No. 60/310,967, filed on Aug. 8, 2001, provisional application No. 60/111,442, filed on Dec. 8, 1998, and provisional application No. 60/107,318, filed on Nov. 6, 1998.

(51) Int. Cl.$^7$ ............................................... B32B 5/16
(52) U.S. Cl. ..................................................... 428/403
(58) Field of Search ........................................... 428/403

(56) References Cited

U.S. PATENT DOCUMENTS

| | | | |
|---|---|---|---|
| 5,939,146 A | * | 8/1999 | Lavernia |
| 6,268,054 B1 | * | 7/2001 | Costantino et al. |
| 6,447,848 B1 | * | 9/2002 | Chow et al. |
| 6,528,029 B1 | * | 3/2003 | Dettling et al. |
| 6,548,171 B1 | * | 4/2003 | Barbera-Guillem et al. |

\* cited by examiner

*Primary Examiner*—H. Thi Le
(74) *Attorney, Agent, or Firm*—Stuart T. Langley; Hogan & Hartson LLP

(57) ABSTRACT

Dispersed phosphor powders are disclosed that comprise nanoscale powders dispersed on coarser carrier powders. The composition of the dispersed fine powders may be oxides, carbides, nitrides, borides, chalcogenides, metals, and alloys. Such powders are useful in various applications such as lamps, cathode ray tubes, field emission displays, plasma display panels, scintillators, X-ray detectors, IR detectors, UV detectors and laser detectors. Nano-dispersed phosphor powders can also be used in printing inks, or dispersed in plastics to prevent forgery and counterfeiting of currency, original works of art, passports, credit cards, bank checks, and other documents or products.

18 Claims, 6 Drawing Sheets

US 6,726,992 B1

NANO-ENGINEERED PHOSPHORS AND RELATED NANOTECHNOLOGY

RELATED APPLICATIONS

The present application is a divisional of copending U.S. patent application Ser. No. 10/004,387 filed on Dec. 4, 2001 entitled "Nano-dispersed powders and methods for their manufacture" which claims the benefit of provisional application No. 60/310,967 filed Aug. 8, 2001 all of which are assigned to the assignee of the present invention and which are incorporated herein by reference.

The present application is also a divisional of copending U.S. patent application Ser. No. 10/150,722 filed on May 17, 2002 entitled "Nanotechnology for Inks and Dopants" which claims the benefit of provisional application No. 60/111,442 filed Dec. 8, 1998 and is a divisional of U.S. patent application Ser. No. 09/274,517 filed on Mar. 23, 1999 entitled "MATERIALS AND PRODUCTS USING NANOSTRUCTURED NON-STOICHIOMETRIC SUBSTANCES" now U.S. Pat. No. 6,344,271 which claims the benefit of provisional application No. 60/107,318, filed Nov. 6, 1998, entitled "Materials and Products Using Nanostructured Non-stoichiometric Materials," all of which are assigned to the assignee of the present invention and which are incorporated herein by reference.

BACKGROUND OF THE INVENTION

1. Field of the Invention

The present invention relates, in general, to nano-dispersed phosphor powders, and, more particularly, to nano-dispersed, complex composition fine powders and methods to produce such powders.

2. Background of the Invention

Powders are used in numerous applications. They are the building blocks of catalytic, electronic, telecommunication, electrical, magnetic, structural, optical, biomedical, chemical, thermal and consumer goods. On-going market demands for more efficient, reliable, smaller, faster, superior and more portable products have demanded miniaturization of numerous products. This, in turn, has demanded miniaturization of the building blocks, i.e. the powders. Sub-micron and nanoscale (or nanosize, ultra-fine) powders, with a size 10 to 100 times smaller than conventional micron size powders, enable quality improvement and differentiation of product characteristics at scales currently unachievable by commercially available micron-sized powders.

Nanopowders in particular, and sub-micron powders in general, are a novel family of materials whose distinguishing features include that their domain size is so small that size confinement effects become a significant determinant of the materials' performance. Such confinement effects can, therefore, lead to a wide range of commercially important properties. Nanopowders, therefore, are an extraordinary opportunity for design, development and commercialization of a wide range of devices and products for various applications. Furthermore, since they represent a whole new family of material precursors where conventional coarse-grain physiochemical mechanisms are not applicable, these materials offer unique combination of properties that can enable novel and multifunctional components of unmatched performance. Bickmore, et al. in U.S. Pat. No. 5,984,997, which along with the references contained therein is incorporated herein by reference, teach some applications of sub-micron and nanoscale powders.

Conventional dispersed powders comprise powders of a first composition (e.g. metal) dispersed on the surface of a carrier which may be of a second composition (e.g. carbon). The dispersed powder structure enables greater and more effective availability of the first composition. It also provides a cost reduction because the second composition can be a low-cost carrier. Additionally, the dispersed powder structure improves the stability and enhances the performance synergistically.

Dispersed powders are desired in a number of applications such as catalysis. The junctions provide active sites for useful chemical reactions. Dispersed powders are often produced using chemical precipitation techniques. These techniques fail to provide a fine and uniform distribution of the dispersed particles on the surfaces of the carrier. Furthermore, the challenge becomes even more difficult when complex compositions need to be dispersed on a carrier powder. Chemical precipitation techniques also leave chemical residues on the surfaces that sometimes are not desirable. Given the difficulty in their production, few dispersed powders are known in the literature and these have found only limited applications.

Phillips in U.S. Pat. No. 5,989,648 (which, along with its references, is specifically incorporated herein by reference) teaches a plasma-based method for preparing metal supported catalysts from an aerosol comprising a mixture of at least one metal powder and at least one support powder. Phillips reports the unusual benefits as catalysts of the metal supported powders so prepared. However, Phillips does not offer motivation for or methods of utilizing fluid precursors to form dispersed powders. Phillips also does not teach nano-dispersed sub-micron powders, motivations for their use, or their benefits to various applications.

SUMMARY OF THE INVENTION

Briefly stated, the present invention involves nano-dispersed powders comprising powders that have been morphologically engineered. More specifically, the term nano-dispersed powders according to this invention refers to powders that have been arranged to provide a desired morphological distribution (dispersion) at nanoscale levels (e.g., sub-100 nm levels). As described in the definition section, nano-dispersed powders comprise carrier particles and attached particles dispersed on the surface of the carrier particles.

The carrier particles may be spherical, non-spherical, porous, tubular, planar, crystallites, amorphous, or any other useful form. The nanoparticles may similarly be one-dimensional, two-dimensional, or three-dimensional, spherical, non-spherical, porous, tubular, planar, crystallites, or amorphous forms, or any other useful form. The attached nano-dispersed particles may be free flowing, agglomerated, porous, coated, or hollow forms or any other useful form. The same carrier may have nanoparticles of more than one composition attached to its surface. In addition, various nano-dispersed particles of different compositions may be blended to achieve useful compositions.

The invention provides nano-dispersed powders with unusually engineered morphology. The unusual morphology provides a high density of multi-phasic points (i.e. points where two or more distinct phases interact with each other and/or species in the gas phase). These morphologically engineered nano-dispersed powders offer benefits to numerous applications. Some illustrative, but non-limiting applications include (a) catalytic transformation of less valuable chemicals and material feed stocks into more valuable chemicals and materials; (b) catalytic transformation of more hazardous chemicals and materials into less hazardous or non-hazardous forms of substances; (c) unusual phosphor, photonic, and optical materials for display, photonic, and optical applications; (d) unusual carriers, tracers, drug delivery vehicles, and markers for biomedical and genomic applications; (e) unusual building blocks for batteries, sensors, and electrochemical products; (f) fillers for polymers, ceramics, and metal matrix composites; and (g) dopants for electronic, magnetic, thermal, piezo, electrical, tooling, structural, inks, paints, and topical health products.

The concept of dispersed powders disclosed and their methods of manufacture may be applied to produce commercially useful submicron and micron dispersed powders as well.

DETAILED DESCRIPTION OF THE INVENTION

The present invention is directed to dispersed powders in general and dispersed nanoscale powders in particular. In a broad sense, dispersed powders provide a structure having a particle size that is largely determined by the size of a carrier particle, and surface behavior that is largely determined by dispersed particles attached to the carrier particle. This somewhat oversimplifies dispersed particle structures in that both the size and ultimate surface behavior may be affected by each component, however the simplification is useful for understanding. With respect to dispersed nanoscale powders in particular, the composite structure can be engineered to have some benefits (e.g., cost, material handling, and the like) associated with larger particle sizes while exhibiting behaviors, particularly surface-related behaviors, of the nanoscale powders dispersed on the carrier.

Figure 1:
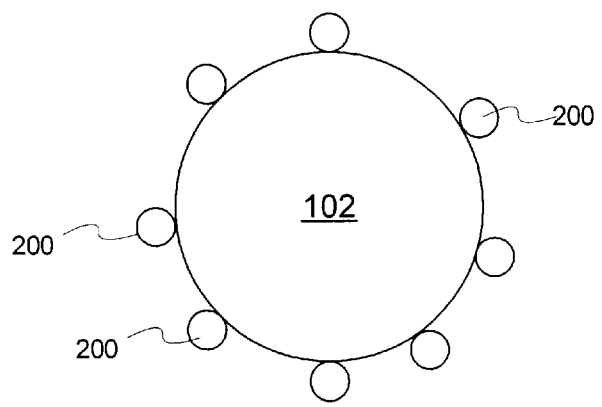
FIG. 1 shows an example of a sub-micron powder comprising nanopowders discretely dispersed on and attached to the surface of the submicron powder.
Figure 2:
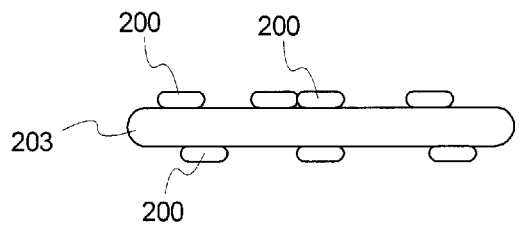
FIG. 2 shows an example of a nanotube carrier having nanoparticles dispersed on and attached to its surface, wherein at least two of the nanoparticles are not in contact with each other.

FIGS. 1 and 2 show two non-limiting examples of nano-dispersed sub-micron powders and nano-dispersed nanopowders, respectively. For example, FIG. 1 shows an example of a sub-micron powder comprising nanopowders 200 discretely dispersed on and attached to the surface of a submicron carrier 102. By "discretely" it is meant that the particles 200 do not touch or overlap. In one sense means particles do not physically overlap. In another sense means that they are sufficiently separate that the solid states of atoms within adjacent particles 200 have a level of interaction determined by their separation. FIG. 2 shows an example of a nanotube carrier 203 having nanoparticles 200 dispersed on and attached to its surface, wherein at least two of the nanoparticles are not in contact with each other.

DEFINITIONS

Certain terms used to describe the invention herein are defined as follows:

"Fine powders" as used herein, refers to powders that simultaneously satisfy the following criteria:

(1) particles with mean size less than 100 microns, preferably less than 10 microns; and (2) particles with aspect ratio between 1 and 1,000,000.

"Submicron powders" as used herein, refers to fine powders that simultaneously satisfy the following criteria:

(1) particles with mean size less than 1 micron; and (2) particles with aspect ratio between 1 and 1,000,000.

The terms "dispersed powders," "morphologically-engineered powders," "decorated powders," and "surface dispersed powders" are used interchangeably and refer to powders that simultaneously satisfy the following criteria:

(1) they comprise at least a first composition that serves as a carrier particle;

(2) they comprise particles of at least a second composition that are attached to the surface of the carrier particle in a mechanically stable state, where the second composition can be the same as or different from the first composition;

(3) the surfaces of the attached particle and carrier particle interact physically, chemically, or electrochemically, but the attached particles exhibit properties that are distinct from the carrier particles;

(4) at least two neighboring attached particles on the surface of the carrier are not in contact with each other at ambient temperature (300 K);

(5) the average separation distance between the center of gravity of the at least two neighboring attached particles on the surface of the carrier that are not in contact with each other is at least 1.05 times the average diameter of the attached particles, preferably greater than 2.5 times the average diameter of the attached particles, more preferably greater than 5 times the average diameter of the attached particles, and most preferably greater than 10 times the average diameter of the attached particles; and (6) the attached particle is smaller than the carrier particle. More particularly, the ratio of the average diameter of the carrier particles and the average diameter of the attached particles is greater than or equal to 2, preferably greater than 10, more preferably greater than 25, and most preferably greater than 100. In one embodiment, the carrier powder is less than 1000 microns, preferably less than 100 microns, more preferably 10 microns, and most preferably 1 micron.

The terms "nanopowders," "nanosize powders," and "nanoscale powders" are used interchangeably and refer to fine powders that simultaneously satisfy the following criteria:

(1) particles having a mean size less than 250 nanometers, preferably less than 100 nanometers; and (2) particles with an aspect ratio between 1 and 1,000,000.

"Pure powders" as used herein, refers to powders that have a composition purity of at least 99.9%, preferably 99.99% by metal basis.

"Nano-dispersed powders" as used herein refers to dispersed powders in which the attached particle is a nanopowder.

"Nano-dispersed sub-micron powders" as used herein refers to dispersed powders in which the attached particle is a nanopowder and the carrier particle is a sub-micron powder.

"Nano-dispersed nanopowders" as used herein refers to dispersed powders where the attached particle is a nanopowder and the carrier particle is also a nanoscale powder.

The terms "powder," "particle," and "grain" are used interchangeably and encompass oxides, carbides, nitrides, borides, chalcogenides, halides, metals, intermetallics, ceramics, polymers, alloys, and combinations thereof. The term includes single metal, multi-metal, and complex compositions. These terms further include hollow, dense, porous, semi-porous, coated, uncoated, layered, laminated, simple, complex, dendritic, inorganic, organic, elemental, non-elemental, composite, doped, undoped, spherical, non-spherical, surface functionalized, surface non-functionalized, stoichiometric, and non-stoichiometric forms or substances. Further, the term powder in its generic sense includes one-dimensional materials (fibers, tubes), two-dimensional materials (platelets, films, laminates, planar), and three-dimensional materials (spheres, cones, ovals, cylindrical, cubes, monoclinic, parallelolipids, dumbbells, hexagonal, truncated dodecahedron, irregular shaped structures, etc.).

The term "aspect ratio" refers to the ratio of the maximum to the minimum dimension of a particle.

The definitions provided above are intended to be applied in the interpretation and understanding of the present invention, and are not necessarily applicable to interpretation of prior art and conventional processes. Some inventive features of the present invention are implicitly expressed in the definitions provided above, and are not to be interpreted as admissions that the defined term is prior art. To the extent these definitions are inconsistent with or more specific than a similar term used in the prior art, it is to be understood that the definition provided herein is preferred in the interpretation of the invention.

The present invention is directed to dispersed powders in general and dispersed nanoscale powders in particular. Dispersed powders preferably simultaneously satisfy the following criteria:

(1) they comprise a carrier particle with at least a first composition;

(2) they comprise particles of at least a second composition that are dispersed on and attached to the surface of the carrier particle in a mechanically stable state (i.e., sufficiently attached to prevent undesired physical mobility during normal use), where the composition of the attached particles may be the same as or different than the carrier particle;

(3) the surfaces of the attached particle and carrier particle interact physically, chemically, or electrochemically with each other, but the attached particles exhibit properties (e.g., electrical properties, chemical properties, solid state properties, size-confinement properties, surface properties and/or the like) that are distinct from the carrier particle;

(4) at least two neighboring attached particles on the surface of the carrier are not in contact with each other at ambient temperature (300 Kelvin);

(5) the average separation distance between the center of gravity of the at least two neighboring attached particles that are not in contact with each other is at least 1.05 times the average diameter of the attached particles, preferably greater than 2.5 times the average diameter of the attached particles, more preferably greater than 5 times the average diameter of the attached particles, and most preferably greater than 10 times the average diameter of the attached particles; and (6) the attached particle is smaller than the carrier particle. More particularly, the ratio of the average diameter of the carrier particles and the average diameter of the attached particles is greater than or equal to 2, preferably greater than 10, more preferably greater than 25, and most preferably greater than 100.

In one embodiment, the carrier particle is a ceramic composition (oxide, carbide, nitride, boride, chalcogenide) or an intermetallic composition (aluminide, silicide) or an elemental composition. Examples of ceramic composition include, but are not limited to (a) simple oxides such as aluminum oxide, silicon oxide, zirconium oxide, cerium oxide, yttrium oxide, bismuth oxide, titanium oxide, iron oxide, nickel oxide, zinc oxide, molybdenum oxide, manganese oxide, magnesium oxide, calcium oxide, and tin oxide; (b) multi-metal oxides such as aluminum silicon oxide, copper zinc oxide, nickel iron oxide, magnesium aluminum oxide, calcium aluminum oxide, calcium aluminum silicon oxide, indium tin oxide, yttrium zirconium oxide, calcium cerium oxide, scandium yttrium zirconium oxide, barium titanium oxide, barium iron oxide and silver copper zinc oxide; (c) doped oxides such as zirconium doped cerium oxide, antimony doped tin oxide, boron doped aluminum oxide, phosphorus doped silicon oxide, and nickel doped iron oxide; (d) carbides such as silicon carbide, boron carbide, iron carbide, titanium carbide, zirconium carbide, hafnium carbide, molybdenum carbide, and vanadium carbide; (e) nitrides such as silicon nitride, boron nitride, iron nitride, titanium nitride, zirconium nitride, hafnium nitride, molybdenum nitride, and vanadium nitride; (f) borides such as silicon boride, iron boride, titanium diboride, zirconium boride, hafnium boride, molybdenum boride, and vanadium boride; (g) complex ceramics such as titanium carbonitride, titanium silicon carbide, zirconium carbonitride, zirconium carboxide, titanium oxynitride, molybdenum oxynitride, and molybdenum carbonitride; and (h) non-stoichiometric ceramics. Other preferred specifications for the carrier particles are provided in Table 1.

TABLE 1

Specifications for the carrier particles

| Parameter | Desired Range | Preferred Range |
| --- | --- | --- |
| Average particle size | 5 nm–5 mm | 50 nm–5 microns |
| Standard deviation of the Size distribution | 1 nm–10 micron | 1 nm–1000 nm |
| Purity, by wt % | Dependant on the needs of the application and cost (normally, greater than 90%) | >99.99% |
| Surface Area | >1 m$^2$/gm | >10 m$^2$/gm |
| XRD crystallite size | Amorphous, 1 nm to >1 micron | <1000 nm |
| Porosity | Dependant on the needs of the application and cost | High |

TABLE 1-continued

Specifications for the carrier particles

| Parameter | Desired Range | Preferred Range |
|---|---|---|
| Composition | Ceramics, elements, alloys | Single metal and multi-metal oxide ceramics |

Preferably, the dispersed particles that are attached to the carrier particle are elemental, ceramic, intermetallic or polymer compositions. The composition of the attached particles can be the same as or different than the composition of the carrier particle. The particles are preferably separated from each other either uniformly or non-uniformly across the surface of the carrier particle. In a particular example, the distance between two neighboring attached particles on the surface of the carrier that do not touch each other is at least 2 Angstroms, but may be greater than 5 Angstroms, 10 Angstroms, 50 Angstroms or more to meet the needs of a particular application.

Examples of elemental compositions for the dispersed, attached particles include, but are not limited to, (a) precious metals such as platinum, palladium, gold, silver, rhodium, ruthenium and their alloys; (b) base and rare earth metals such as iron, nickel, manganese, cobalt, aluminum, copper, zinc, titanium, samarium, cerium, europium, erbium, and neodymium; (c) semi-metals such as boron, silicon, tin, indium, selenium, tellurium, and bismuth; (d) non-metals such as carbon, phosphorus, and halogens; (e) clusters such as fullerenes ($C_{60}$, $C_{70}$, $C_{82}$), silicon clusters, and nanotubes of various compositions; and (f) alloys such as steel, shape memory alloys, aluminum alloys, manganese alloys, and superplastic alloys.

Examples of ceramic compositions for the dispersed, attached particles include, but are not limited to, (a) simple oxides such as aluminum oxide, silicon oxide, zirconium oxide, cerium oxide, yttrium oxide, bismuth oxide, titanium oxide, iron oxide, nickel oxide, zinc oxide, molybdenum oxide, manganese oxide, magnesium oxide, calcium oxide, and tin oxide; (b) multi-metal oxides such as aluminum silicon oxide, copper zinc oxide, nickel iron oxide, magnesium aluminum oxide, calcium aluminum oxide, calcium aluminum silicon oxide, indium tin oxide, yttrium zirconium oxide, calcium cerium oxide, scandium yttrium zirconium oxide, barium titanium oxide, and silver copper zinc oxide; (c) doped oxides such as zirconium doped cerium oxide, antimony doped tin oxide, boron doped aluminum oxide, phosphorus doped silicon oxide, and nickel doped iron oxide; (d) carbides such as silicon carbide, boron carbide, iron carbide, titanium carbide, zirconium carbide, hafnium carbide, molybdenum carbide, and vanadium carbide; (e) nitrides such as silicon nitride, boron nitride, iron nitride, titanium nitride, zirconium nitride, hafnium nitride, molybdenum nitride, and vanadium nitride; (f) borides such as silicon boride, iron boride, titanium diboride, zirconium boride, hafnium boride, molybdenum boride, and vanadium boride; (g) complex ceramics such as titanium carbonitride, titanium silicon carbide, zirconium carbonitride, zirconium carboxide, titanium oxynitride, molybdenum oxynitride, and molybdenum carbonitride; and (h) non-stoichiometric ceramics.

The nano-dispersed powders of this invention may further comprise carrier particles having dispersed particles of more than one composition dispersed on and attached to their surfaces. In addition, the dispersed powders may comprise multiple layers of the attached particles, where the layers may be concentric or non-concentric. Other preferred specifications for the carrier particles are provided in Table 2.

TABLE 2

Specifications for dispersed, attached particles

| Parameter | Desired Range | Preferred Range |
|---|---|---|
| Average particle size | Less than 5 micron | 1 nm–250 nm |
| Standard deviation of the Size distribution | 1 nm–750 nm | 1 nm–50 nm |
| Purity, by wt % | Dependant on the needs of the application and cost (normally, greater than 90%) | >99.99% |
| Surface Area | 1 $m^2$/gm | >100 $m^2$/gm |
| XRD crystallite size | Amorphous, 1 nm to 1 micron | <250 nm |
| Mechanical Stability | Dependant on the needs of the application and cost | High |

The distinctive features that make nano-dispersed powders of this invention commercially desirable result in part from (a) the separation between the attached nanoparticles during their use, (b) the unusual properties of attached nanoparticles, (c) the useful interaction between the carrier composition and the dispersed attached particles, and (d) the morphologically induced interaction of dispersed attached particle interfaces and the carrier particle interface with the chemical, electromagnetic, electrochemical, photonic, magnetic, charges, and thermodynamic environment around the dispersed particles.

More specifically, the distinct usefulness of nano-dispersed powders is in part a result of the separation between the dispersed nanoparticles attached to the surface of the carrier particle, which in turn reduces the potential sintering of the particles at higher temperatures. It is known in the art that closely packed small particles in general, and nanoscale particles in particular, sinter faster as the temperature of use increases. This limits the time during which the useful performance of the particle is available. Many applications, particularly those that operate at high temperatures (e.g. catalysis), require that the surface and bulk properties of the material in use do not vary or that they vary only slightly with time. This is difficult to accomplish with closely packed nanoparticles, because such nanoparticles sinter (diffuse and grow) across the grain boundaries as a function of temperature and time. By dispersing the nanoparticles on the surface of the carrier particle, the surfaces of the dispersed nanoparticles are kept from touching each other. This reduces or eliminates the interaction and consequent sintering between the nanoparticles, even at high temperatures. As a result, the interaction at the grain boundary is eliminated, and consequently the time and temperature based variances are eliminated. Thus, dispersing the nanoparticles solves an outstanding problem that confronts attempts to utilize the beneficial properties of nanoscale powders.

The distinct usefulness of nano-dispersed powders is also in part a result of the unusual inherent properties of nano-scaled particles. Nano-scaled materials are a family of materials whose distinguishing feature is that their mean grain size is less than 100 nm. Nanopowders, because of their nanoscale dimensions (near-molecular), feature a variety of confinement effects that significantly modify the properties of the material. The physics behind this has been aptly conjectured to be the following: a property will be altered when the entity or mechanism responsible for that property is confined within a space smaller than the critical length associated with that entity or mechanism. Such confinement effects lead to very desirable properties. For example:

(a) nanopowders have a very high surface area which leads to enhanced interfacial diffusivities and thus enables rapid, low temperature formation of materials that are typically difficult to process;

(b) nanopowders are isomorphic because of dimensional confinement. Furthermore, enhanced solubilities are observed leading to non-equilibrium compositions. This leads to catalysts and reactants with extremely high surface areas, high selectivity and activity;

(c) nanopowders have grain sizes that are too small for Frank-Read dislocation to operate in the conventional yield stress domain; consequently, enhancement in strengths and hardness of 100% to 500% are observed in films and pellets made from nanopowders;

(d) the size of the nanopowder is less than the wavelength of visible light; consequently unique optical materials with grain sizes tailored for excitonic interactions with particular wavelengths can be prepared;

(e) nanopowders are confined to a dimension less than the mean free path of electrons; consequently, unusual electrical and electrochemical properties can be observed;

(f) nanopowders are confined to dimension less than the domain size of magnetic materials; consequently, nanopowders are precursors to magnetic materials exhibiting Giant Magnetoresistive (GMR) and superparamagnetic effects; and (g) nanopowders feature quantum confinement to dimensions less than Debye length. This leads to electrochemical properties with order of magnitude higher sensitivities to chemical species.

Nanopowders in general, and nano-dispersed powders in particular, thus provide an extraordinary opportunity for design, development and commercialization of a wide range of structural, electrochemical, electrical, optical, electronic, magnetic and chemical applications. Furthermore, since nanopowders represent a whole new family of material precursors for which conventional coarse-grain physiochemical mechanisms are not performance determining, nanomaterials in general and nano-dispersed powders in particular offer unique combination of properties that can enable novel and multifunctional components of unmatched performance.

Yet another source of distinct usefulness of nano-dispersed powders results in part from the useful interaction between the dispersed attached nanoparticles and the carrier particles. Dimensionally confined nanomaterials have properties that are determined in part by the interface thermodynamics and characteristics. These interfaces in turn are influenced by neighboring atoms. By dispersion, the nanoparticles interact with the interface of the carrier particles. This interaction can induce a novel performance that is not exhibited by either of the carrier particle or nanoparticle materials in isolation.

Yet another source of distinct usefulness of nano-dispersed powders results in part from the high concentration of triple points. Triple points are the points where three or more phases meet and lead to useful interaction between the dispersed particles, the carrier particles, and the fluid environment around the junction of dispersed and carrier particles. The nanoscale size of dispersed particles significantly increases the density of triple points. These are points where useful chemical, electrochemical, physical, electronic, photonic and electrical interactions can occur.

1. Methods of Producing Nano-dispersed Powders

Figure 3:
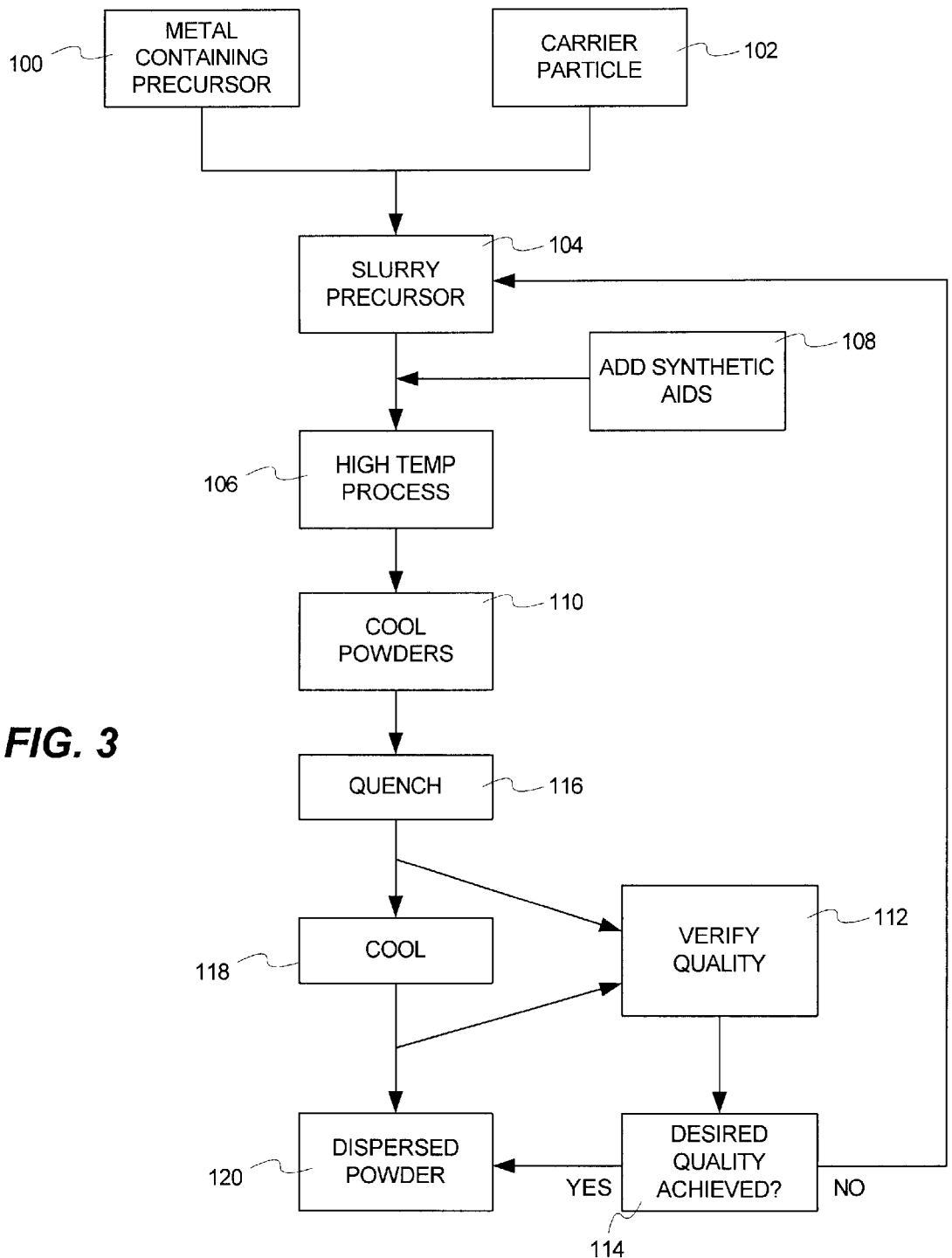
FIG. 3 shows one embodiment for producing nano-dispersed powders by combining a metal precursor and carrier particles.

FIG. 3 shows one embodiment of a system for producing dispersed powders in accordance with the present invention. This method can be used to produce dispersed powders that are coarse and pure, but is particularly useful for nano-dispersed sub-micron and nano-dispersed nanoscale powders.

The process shown in FIG. 3 begins at 100 with a metal-containing precursor such as an emulsion, fluid, particle-containing liquid slurry, or water-soluble salt. The precursor may be a gas, a single-phase liquid, a multi-phase liquid, a melt, fluid mixtures, or combinations thereof. The metal-containing precursor comprise a stoichiometric or a non-stoichiometric metal composition wherein at least some portion is in a fluid phase. Fluid precursors are preferred in this invention over solid precursors because fluids are easier to convey, evaporate, and thermally process, and the resulting product is more uniform.

In one embodiment of this invention, the precursors are preferably environmentally benign, safe, readily available, high-metal loading, lower cost fluid materials. Examples of metal-containing precursors suitable for purposes of this invention include, but are not limited to, metal acetates, metal carboxylates, metal ethanoates, metal alkoxides, metal octoates, metal chelates, metallo-organic compounds, metal halides, metal azides, metal nitrates, metal sulfates, metal hydroxides, metal salts soluble in organics or water, and metal-containing emulsions.

In another embodiment, multiple metal precursors may be mixed if complex nano-dispersed powders are desired. For example, a barium precursor and iron precursor may be mixed to prepare high purity barium ferrite powders. As another example, a yttrium precursor, barium precursor, and copper precursor may be mixed in correct proportions to yield a high purity YBCO powder for superconducting applications. In yet another example, an aluminum precursor and silica precursor may be mixed to yield aluminum silicate powders. Such complex nano-dispersed powders can help create materials with surprising and unusual properties not available through the respective single metal oxides or a simple nanocomposite formed by physical blending powders of different compositions. To illustrate, nanoscale powders formed from blending two or more metals can create materials with a hardness, refractive index, or other property or a combination of such properties that have values that are intermediate to the properties of the respective single metal oxide forms. As an example, complex powders may be prepared from aluminum and silicon precursors to create novel aluminum silicate nanomaterials with refractive index that is intermediate to the refractive index of the alumina and silica.

In all embodiments of this invention, it is desirable to use precursors of a higher purity to produce a nano-dispersed powder of a desired purity. For example, if purities greater than x% (by metal basis) is desired, one or more precursors that are mixed and used have purities greater than or equal to x% (by metal basis) to practice the teachings herein.

With continued reference to FIG. 3, the metal-containing precursor 100 (containing one or a mixture of metal-containing precursors) is mixed with carrier particles 102 of desired size, composition, and characteristics. Carrier particles 102 may comprise micron-sized particles, sub-micron particles, or nanostructured particles. The resultant slurry precursor 104 is the preferred feed material for producing nano-dispersed powders. The relative concentrations of the metal-containing precursors 100 and the carrier particles 102 should be substantially equivalent to that desired in the final product.

Upon formation of the slurry precursor 104, the slurry precursor 104 is fed into a high temperature process 106 implemented using a high temperature reactor, for example. In one embodiment, a synthetic aid such as a reactive fluid 108 can be added along with the slurry precursor 104 as it is being fed into the reactor 106. For example, when the object is to prepare a nano-dispersed powder comprising a dispersed oxide, a preferred embodiment of this invention is to use a precursor 100 in which the oxygen-to-carbon elemental ratio in the precursor molecule is high. Alternatively, or in addition, a reactive fluid 108 that provides excess oxygen may be added along with the slurry precursor 104 to the reaction zone 106. Examples of such reactive fluids include, but are not limited to, oxygen gas and air.

As another example, when the object is to prepare a nano-dispersed powder comprising a dispersed carbide, a preferred embodiment of this invention is to use a precursor 100 in which the oxygen-to-carbon elemental ratio is less than 0.1, more preferably less than 1.0, and most preferably less than 2.0. Alternatively, or in addition, a reactive fluid 108 that provides excess carbon or reduces excess oxygen may be added along with the slurry precursor 104 to the reaction zone 106. Examples of such reactive fluids include, but are not limited to, methane, ethylene, acetylene, ethane, natural gas, benzene, naphtha, and hydrogen.

As another example, when the object is to prepare a nano-dispersed powder comprising a dispersed nitride, a preferred embodiment of this invention is to use a precursor 100 in which the oxygen-to-nitrogen elemental ratio in the precursor molecule less than 0.1, more preferably less than 1.0, and most preferably less than 2.0. Alternatively, or in addition, a reactive fluid 108 that provides excess nitrogen or reduces excess oxygen may be added along with the slurry precursor 104 to the reaction zone 106. Examples of such reactive fluids include, but are not limited to, amines, ammonia, hydrazine, nitrogen, and hydrogen.

As another example, when the object is to prepare a nano-dispersed powder comprising a dispersed boride, a preferred embodiment of this invention is to use a precursor 100 in which the oxygen-to-boron elemental ratio in the precursor molecule less than 0.1 and more preferably less than 1.0, and most preferably less than 1.5. Alternatively, or in addition, a reactive fluid 108 that provides excess boron or reduces excess oxygen may be added along with the slurry precursor 104 to the reaction zone 106. Examples include, but are not limited to, boranes, boron, and hydrogen.

As another example, when the object is to prepare a nano-dispersed powder comprising a dispersed carbonitride, a preferred embodiment of this invention is to use a precursor 100 in which the (a) oxygen-to-carbon elemental ratio in the precursor molecule less than 0.1 and more preferably less than 1.0, and most preferably less than 2.0, and (b) the oxygen-to-nitrogen elemental ratio in the precursor molecule less than 0.1, more preferably less than 1.0, and most preferably less than 2.0. Alternatively, or in addition, a reactive fluid 108 may be added along with the slurry precursor 104 to the reaction zone 106. Examples of such reactive fluids include, but are not limited to, methane, ethylene, acetylene, ethane, natural gas, benzene, naphtha, amines, ammonia, hydrazine, nitrogen, and hydrogen.

While the above examples specifically teach methods of preparing dispersed powders of oxides, carbides, nitrides, borides, and carbonitrides, the teachings may be readily extended in an analogous manner to other compositions such as chalcogenides. While it is preferred to use high temperature processing, a moderate temperature processing or a low/cryogenic temperature processing may also be employed to produce high purity nano-dispersed powders.

The precursor 100 may be also pre-processed in a number of other ways before the high temperature thermal treatment. For example, the pH may be adjusted to ensure stable precursor. Alternatively, selective solution chemistry such as precipitation may be employed to form a sol or other state of matter. The precursor 101 may be pre-heated or partially combusted before the thermal treatment.

The slurry precursor 104 may be injected axially, radially, tangentially, or at any other angle into the high temperature region 106. As stated above, the slurry precursor 104 may be pre-mixed or diffusionally mixed with other reactants. The slurry precursor 104 may be fed into the thermal processing reactor by a laminar, parabolic, turbulent, pulsating, sheared, or cyclonic flow pattern, or by any other flow pattern. In addition, one or more metal-contain ring precursors 100 can be injected from one or more ports in the reactor 106. The feed spray system may yield a feed pattern that envelops the heat source or, alternatively, the heat sources may envelop the feed, or alternatively, various combinations of this may be employed. A preferred embodiment is to atomize and spray the feed in a manner that enhances heat transfer efficiency, mass transfer efficiency, momentum transfer efficiency, and reaction efficiency. The reactor shape may be cylindrical, spherical, conical, or any other shape. Methods and equipment such as those taught in U.S. Pat. Nos. 5,788,738, 5,851,507, and 5,984,997 (each of which is specifically incorporated herein by reference) can be employed in practicing the methods of this invention.

With continued reference to FIG. 3, after the slurry precursor 104 has been fed into reactor 106, it is processed at high temperatures to form the product nano-dispersed powder. The thermal treatment is preferably done in a gas environment with the aim to produce a product such as powders that have the desired porosity, strength, morphology, dispersion, surface area, and composition. This step produces by-products such as gases. To reduce costs, these gases may be recycled, mass/heat integrated, or used to prepare the pure gas stream desired by the process.

The high temperature processing is conducted at step 106 (FIG. 3) at temperatures greater than 1500° C., preferably 2500° C., more preferably greater than 3000° C., and most preferably greater than 4000° C. Such temperatures may be achieved by various methods including, but not limited to, plasma processes, combustion, pyrolysis, electrical arcing in an appropriate reactor, and combinations thereof. The plasma may provide reaction gases or just provide a clean source of heat.

An outstanding problem with conventional nanopowder synthesis methods is broad size distribution. This may happen because of non-uniformities in heat, mass, and/or momentum transfer. One reason for such non-uniformities is the sudden drop in temperature and reacting species at the outer edge of the reaction front such as a combustion flame. An illustration of outer edge of a flame would be the outer perimeter of the cross section of the flame, i.e. plane perpendicular to the direction of flame flow. At these edges, the reaction pathways are influenced by the heat and mass and momentum boundary conditions. This zone, therefore, yields conditions where the product produced is non-uniform and therefore different than those produced inside the boundary. Such conditions apply to all sorts of high temperature flow fields including flames and are created by various types of burners or reactor system. Some illustrations of such burners are taught by R. M. Fristrom (in *Flame Structure and Processes*, Oxford University Press, New York, 1995, which along with references contained therein is specifically incorporated herein by reference).

Figure 4:
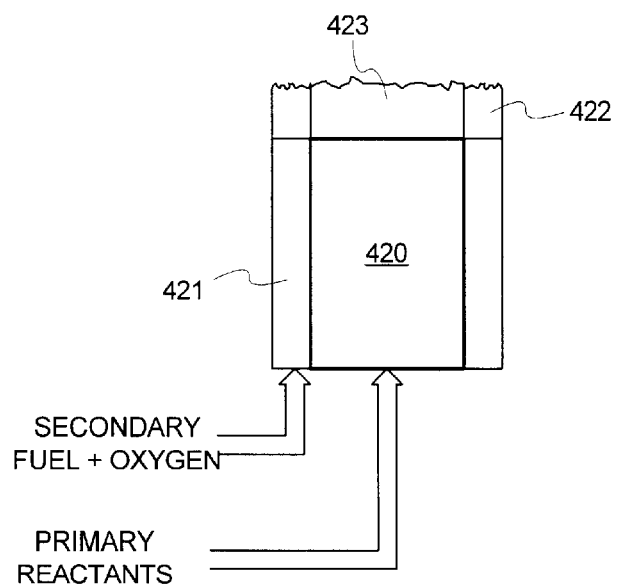
FIG. 4 shows a schematic concentric flame approach to improve the uniformity of particle size distribution.

One feature of this invention is the ability to reduce this non-uniformity by eliminating or reducing the above-described source of non-uniformity. This can be accomplished in many ways. As an illustration, the reaction zone (such as a combustion flame) can be surrounded by a fully or a partially concentric zone of a medium with a thermal, mass and momentum profile that reduces such non-uniformity. For example, FIG. 4 shows a primary combustion burner 420, over which useful particle producing flame chemistry occurs, is preferably surrounded by a concentric secondary burner 421 where a fuel is burned to maintain the outer edge temperatures in region 422 as close to the primary flame's highest temperature in region 423 as possible. To the extent possible, the mass and momentum profile of the medium created by the concentric secondary burner 421 should be similar in one or more respects to the mass and momentum profile of the medium created by the primary burner 420. Such concentric burners can assist in a more uniform thermal, mass, and momentum profile for the reaction space created by the primary burner 420. A non-limiting illustration of such concentric burners is discussed and referenced by Howard et al., Carbon 30(8):1183–1201 (1992), which along with references contained therein is specifically incorporated herein by reference.

In another embodiment the slurry precursor 104 is pre-treated to minimize non-uniformity in heat, mass, and/or momentum transfer. This can be achieved through techniques such as (a) axially, radially, or tangentially surrounding the high temperature processing zone 106 with an inert gas plasma, (b) axially, radially, or tangentially surrounding the high temperature processing zone 106 with a complete combustion flame, preferably of high temperature, or (c) axially, radially, or tangentially surrounding the high temperature processing zone 106 with an electrical arc or high temperature radiation source. The concentric flame's adiabatic temperature (or concentric thermal zone) is preferably greater than 500° C., more preferably greater than 1000° C., and most preferably greater than 2000° C. The minimal requirement of this technique is that the high temperature processing zone temperature at the outer edges be higher when the concentric high temperature thermal zone is present than when it is absent.

This principle of concentric thermal zones can be applied to any method of producing dispersed powders. Illustrative examples of processes where this principle can be used include one-dimensional combustion flames, diffusion flames, turbulent flames, pre-mixed flames, flat flames, plasma, arcing, microwave, sputtering, pyrolysis, spray evaporation, laser and hydrothermal processing.

In the embodiment shown in FIG. 3, carrier particles 102 are present in the high temperature process. The carrier particles 102 may be substantially inert during high temperature process 106, or they may be transformed by physical, chemical, or solid state reactions. High temperature processing is performed in a manner such that the end product of high temperature process 106 includes carrier particles 102 of desired size, composition and uniformity. Alternatively, the carrier particles can be added at a later stage of the high temperature process.

The high temperature process 106 results in a vapor comprising fine powders and carrier particles. After the thermal processing, this vapor is cooled at step 110 to nucleate dispersion of fine powders, preferably nanopowders, onto the surface of the carrier particles. Preferably, the cooling temperature at step 110 is high enough to prevent moisture condensation. The dispersed particles are formed from the precursor because of the thermokinetic conditions in the process. By engineering the process conditions such as pressure, residence time, flow rates, species concentrations, diluent addition, degree of mixing, momentum transfer, mass transfer, and heat transfer, the morphology of the dispersed powders can be tailored. It is important to note that the focus of the process is on producing a dispersed powder product that excels in satisfying the end application requirement and customer needs. In some cases, this may be achieved with uniformly dispersed particles and in others it may be non-uniformly distributed particles that best meet the customer needs.

After cooling, the nano-dispersed powder is preferably quenched to lower temperatures at step 116 to minimize and preferably prevent agglomeration or grain growth. Suitable quenching methods include, but are not limited to, methods taught in U.S. Pat. No. 5,788,738. It is preferred that quenching methods be employed which can prevent deposition of the powders on the conveying walls. These methods may include electrostatic means, blanketing with gases, the use of higher flow rates, mechanical means, chemical means, electrochemical means, or sonication/vibration of the walls.

In one embodiment, the high temperature processing system includes instrumentation 112, 114 that can assist in the quality control of the process by analyzing the quality of the product either between steps 116 and 118, or between steps 118 and 120. The data collected after analysis of the product can provide information on how to adjust the process variables to adjust the quality of the product.

It is preferred that the high temperature processing zone 106 is operated to produce fine powders 120 (FIG. 3), preferably submicron powders, and most preferably nanopowders. The gaseous products from the process may be monitored for composition, temperature and other variables to ensure quality at 112 (FIG. 3). The gaseous products may be recycled to be used in process 108 (FIG. 3), or used as a valuable raw material when dispersed powders 120 have been formed. Following quenching step 116 (FIG. 3) the nano-dispersed powders are cooled further at step 118 and then harvested at step 120.

The product nano-dispersed powders 120 may be collected by any method. Suitable collection means include, but are not limited to, bag filtration, electrostatic separation, membrane filtration, cyclones, impact filtration, centrifugation, hydrocyclones, thermophoresis, magnetic separation, and combinations thereof.

Figure 5:
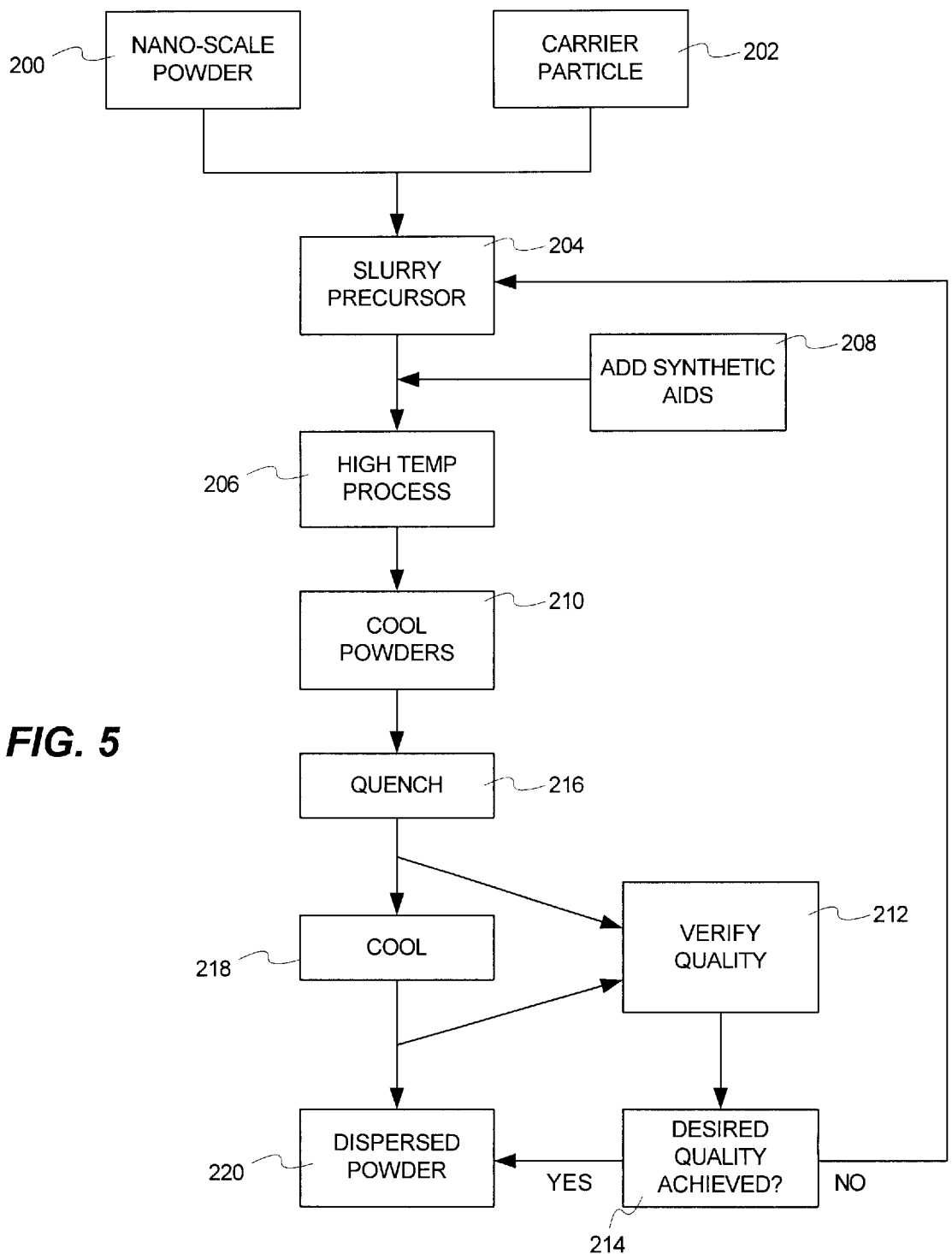
FIG. 5 shows an alternate embodiment for producing nano-dispersed particles in which both the nano-sized powders and the carrier particles are prepared in-situ during the thermal processing.

FIG. 5 shows an alternate embodiment for producing dispersed particles according to this invention. The embodiment shown in FIG. 5 begins with nano-scale powders 200 produced by any technique. These nanoscale powders 200 are mixed with desired coarser carrier particles 202 into a slurry precursor 204. The slurry precursor 204 is mixed with a fluid such as a fuel and then used as precursor to make nano-dispersed particles following steps 204–210 in a manner similar to that described for steps 104–112 of FIG. 3.

Alternatively, precursors may be blended into or emulsified into a commercially available nanoparticulate sol, such as NALCO® silica sols or NYACOL® alumina sol. This multi-phased feed is then used to make particles by the process described by FIG. 5.

Figure 6:
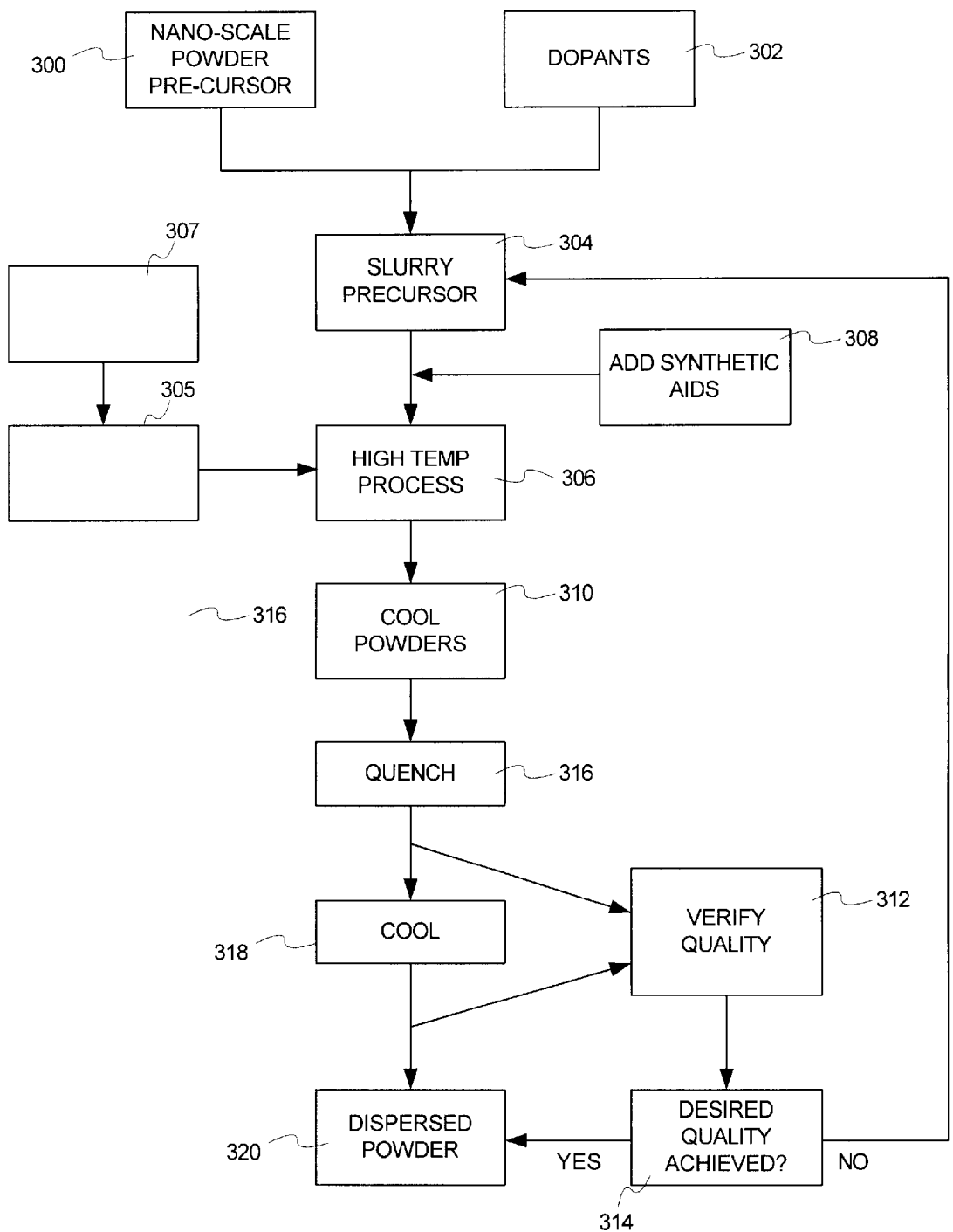
FIG. 6 shows an alternate embodiment for producing nano-dispersed powders by combining a metal precursor and carrier particles.

FIG. 6 shows yet another embodiment for producing dispersed particles according to this invention. In this method, both the nano-scale particles and the carrier particles are formed in-situ during the thermal processing step. More specifically, a metal-containing precursor 300 (containing one or a mixture of metal-containing precursors) and optional dopants 301 are combined to form a precursor batch 302. The dopants may be added to modify or enable the performance of the dispersed powders suitably for a particular application. Such dopants include, but are not limited to, transition metals, rare earth metals, alkali metals, alkaline earth metals, semi-metals, and non-metals. It is preferred that, like other metal precursors, precursors for such dopants are intimately mixed with the metal-containing precursor 300. It is also preferred that dopant precursors are fluids. The precursor batch is then feed into a high temperature reactor 306. In one embodiment, one or more synthetic aids such as a reactive fluid 308 can be added along with the precursor batch 302 as it is being fed into the reactor 306. Examples of synthetic aids include, but are not limited to, oxygen, methane, nitrogen, feed gases, oxidants, or reactants.

With continued reference to FIG. 6, the precursor batch 302 is then fed into a thermal reactor 306 where the precursors are partially transformed, or preferably completely transformed, into the vapor form. The source of thermal energy in the preferred embodiments is plasma generator 305. Plasma gas 307, which may be inert or reactive, is supplied to plasma generator 305. Alternatively, the source of thermal energy may be internal energy, heat of reaction, conductive, convective, radiative, inductive, microwave, electromagnetic, direct or pulsed electric arc, laser, nuclear, or combinations thereof, so long as it is sufficient to cause the rapid vaporization of the powder suspension being processed.

The high temperature process 306 results in a vapor comprising both fine powders and carrier particles formed in-situ from the precursors 300. In order to produce both the dispersed and carrier particles, the thermokinetic conditions and ratio of the precursor to the synthetic aid are controlled. Alternatively, the precursors can be fed at different locations in the reactor to engineer the residence time experienced by each feed location. A change in residence time or thermokinetic condition or process variable produces powders of different characteristics (size, shape, composition, etc.). This method can therefore be employed to produce both carrier and attached particles. After the thermal processing, this vapor is cooled at step 310 to nucleate dispersion onto the surface of the carrier particles. Preferably, the cooling temperature at step 310 is high enough to prevent moisture condensation.

With continued reference to FIG. 6, after cooling step 310 the nano-dispersed powder is preferably quenched as described above to lower temperatures at step 316 to prevent agglomeration or grain growth. It is preferred that quenching methods be employed which can prevent deposition of the powders on the conveying walls. Following quenching step 316 the nano-dispersed powders are cooled further at step 318 and then harvested at step 320. The product of this process is a dispersed powder, such as nano-scale particles dispersed on larger nano-scale particles or nano-scale particles dispersed on sub-micron particles.

In yet another embodiment (not shown), the nano-dispersed powders are produced by first combining nano-scale powders produced by any method with carrier particles. The relative concentrations of the nano-scale powder and the carrier particles should be substantially equivalent to that desired in the final product. The mixture is then mechanically milled by methods known in the art to produce the nano-dispersed powders. The milling may be done in gas or liquid environment. If a liquid environment is employed, the liquid may comprise acids, alkalis, oxidizers, dispersants, metal containing precursors, or other suitable constituents.

Figure 7:
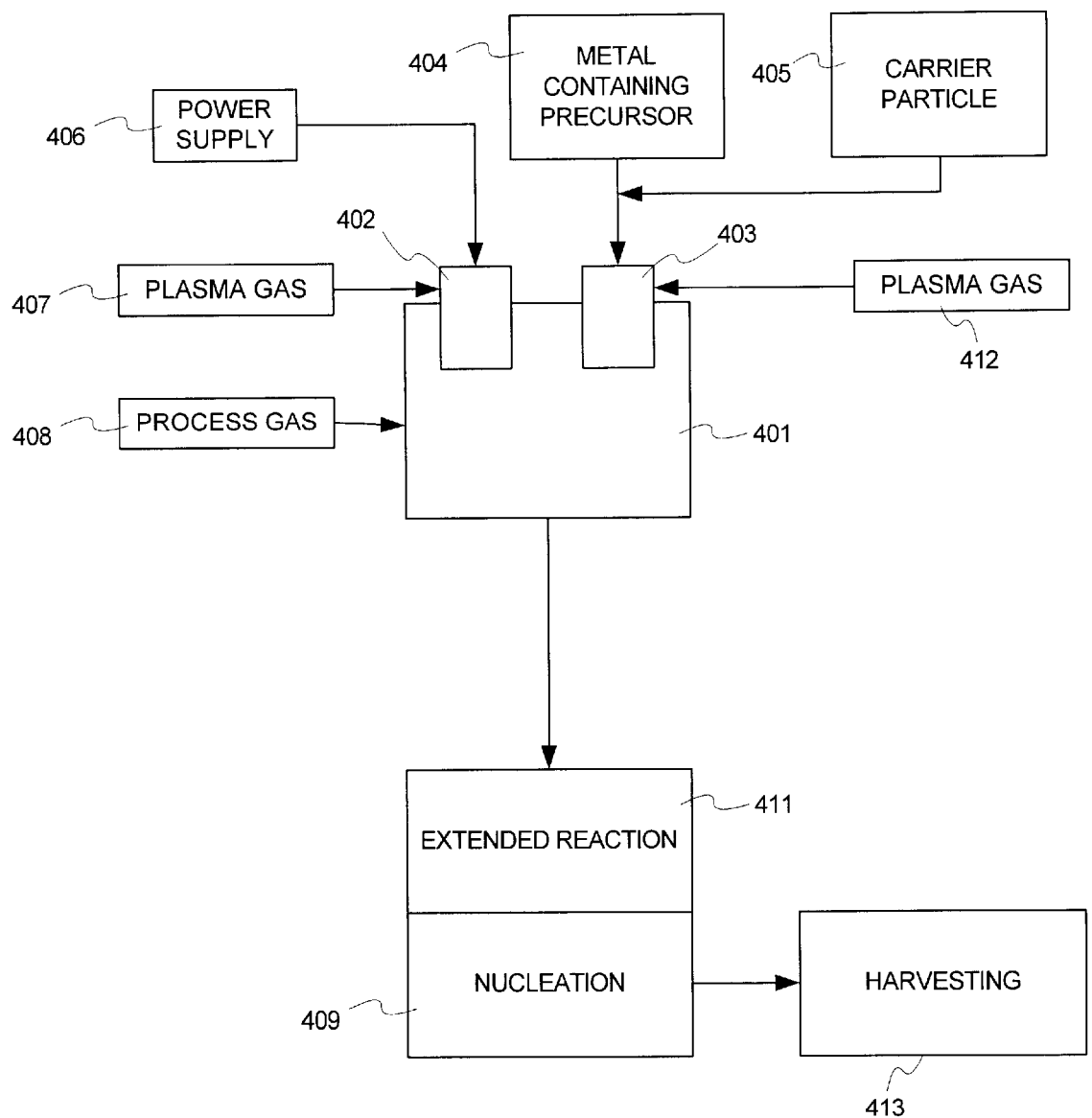
FIG. 7 shows an alternate embodiment for producing nano-dispersed powders by combining a metal precursor and carrier particles.
Figure 8:
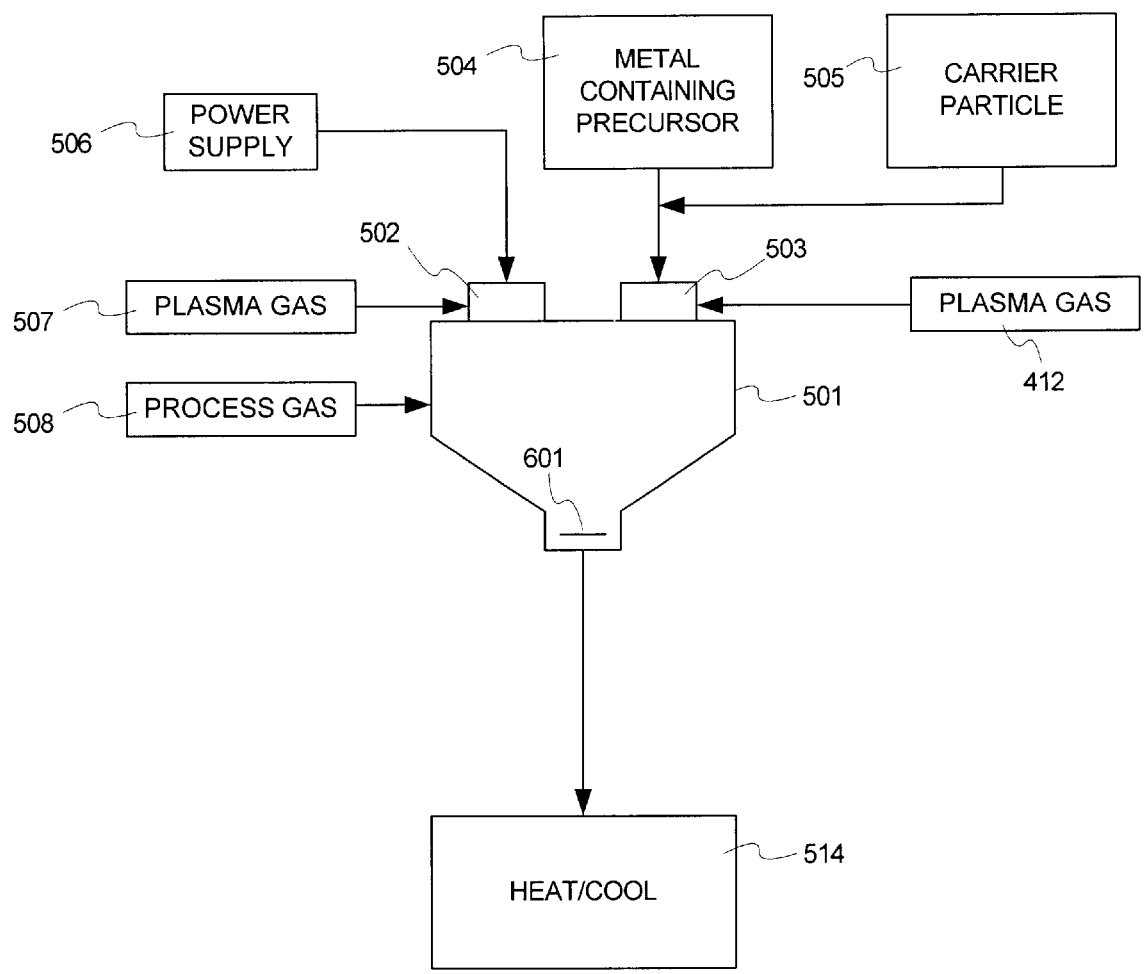
FIG. 8 shows an alternate embodiment for producing nano-dispersed powders by combining a metal precursor and carrier particles.

FIG. 7 shows an alternative flow diagram of a thermal process for the synthesis of nano-dispersed powders. In this method, precursors 404 such as metal containing emulsions, fluid, or water-soluble salt, are combined with carrier particles 405. Although a single precursor storage tank 404 is shown in FIG. 7, it is to be understood that multiple precursor tanks may be provided and used with or without premixing mechanisms (not shown) to premix multiple precursors before feeding into reactor 401.

In one embodiment, a feed stream of precursor material from storage tank 404 and carrier particles 405 is atomized in mixing apparatus 403. Alternatively, a precursor storage 404 may be implemented by suspending the precursor in a gas, preferably in a continuous operation, using fluidized beds, spouting beds, hoppers, or combinations thereof, as best suited to the nature of the precursor.

The resulting suspension is advantageously preheated in a heat exchanger (not shown), preferably with the exhaust heat, and is then fed into a thermal reactor 401 where the atomized precursors are partially transformed, or preferably completely transformed, into the vapor form. The source of thermal energy in the preferred embodiments is plasma generator 402 powered by power supply 206. Plasma gas 407, which may be inert or reactive, is supplied to plasma generator 402. Alternatively, the source of thermal energy may be internal energy, heat of reaction, conductive, convective, radiative, inductive, microwave, electromagnetic, direct or pulsed electric arc, laser, nuclear, or combinations thereof, so long as it is sufficient to cause the rapid vaporization of the precursor being processed. The peak temperature in the thermal reactor 401 is greater than 1500° C., preferably greater than 2500° C., more preferably greater than 3000° C., and most preferably greater than 4000° C. Optionally, in order to prevent contamination of the vapor stream caused by partial sublimation or vaporization, the walls of reactor 401 may be pre-coated with the same material being processed.

The vapor next enters an extended reaction zone 411 of the thermal reactor which provides additional residence time as needed to complete the processing of the feed material and to provide additional reaction and forming time for the vapor (if necessary). As the stream leaves the reactor, it passes through a zone 409 where the thermokinetic conditions favor the nucleation of solid powders from the vaporized precursor. These conditions are determined by calculating the supersaturation ratio and critical cluster size required to initiate nucleation. Rapid quenching leads to high supersaturation which gives rise to homogeneous nucleation. The zones 401, 411, and 409 may be combined and integrated in any manner to enhance material, energy, momentum, and/or reaction efficiency.

As soon as the vapor has begun nucleation, the process stream is quenched in a heat removal apparatus within nucleation zone 409 comprising, for example, a converging-diverging nozzle-driven adiabatic expansion chamber at rates at least exceeding 1,000 K/sec, preferably greater than 1,000,000 K/sec, or as high as possible. A cooling medium (not shown) may be utilized for the converging-diverging nozzle to prevent contamination of the product and damage to the expansion chamber.

The quenched gas stream is filtered by appropriate separation equipment in harvesting region 413 to remove the nano-dispersed product from the gas stream. As is well understood in the art, the filtration can be accomplished by single stage or multistage impingement filters, electrostatic filters, screen filters, fabric filters, cyclones, scrubbers, magnetic filters, or combinations thereof. The filtered nano-dispersed product is then harvested from the filter, either in batch mode or continuously, using screw conveyors or gas-phase solid transport, and the product stream is conveyed to powder processing or packaging unit operations (not shown).

The process is preferably operated at near ambient pressures and more preferably at pressures that are less than 750 mm Hg absolute (i.e. vacuum). Such a low pressure can be achieved using any type of vacuum pump, compressor, and more preferably using compressed fluid-based eductor operating on a venturi principle given the lower cost, simplicity and environmental benefits. Vacuum generating equipment may be placed at any stage of the overall process. The product stream from the vacuum generating equipment may be utilized elsewhere in the process to achieve heat and mass integration and thereby to reduce costs. For example, in one embodiment a suspension or dispersion may be prepared in a liquid directly if the liquid were to be utilized as the high pressure driving fluid for the eductor.

In an alternate embodiment shown in FIG. 8, rather than harvesting the nano-dispersed product, the nano-dispersed product is deposited directly on a substrate 601 to form a coating or film or near-net shape structural part. In this embodiment, the fluid precursor 504 and carrier particles 505 are fed into mixing apparatus 503 and then fed into a thermal reactor 501 where the atomized precursors are partially transformed, or preferably completely transformed, into the vapor form.

The preferred source of thermal energy in the embodiment illustrated in FIG. 8 is plasma generator 502 powered by power supply 506. The mixture is thermally heated in reactor 501 to high temperatures to yield a hot vapor. A substrate 601 having an exposed surface is provided within or in communication with reaction chamber 501 on, for example, a thermally controlled substrate holder. The hot vapor is then contacted with the exposed substrate surface and coats the exposed surface. The hot vapor may be cooled or quenched before the deposition step to provide a stream that has fine liquid droplets or hot particulate matter. The substrate 601 may be cooled or heated using a substrate thermal control 514 to affect the quality of the coating.

The substrate 601 may be mounted on a turn-table or drum to rotate the substrate 601 parallel, perpendicularly, tangentially (or at any other angle) relative to the gas stream comprising of nanoparticles. The rotation can help achieve different thickness, a conformal form, or a curved form. The substrate 601 to be coated may be continuously fed and removed over rotating cylinders to substrate 601. By controlling the substrate feed rate, the coating thickness can be controlled. Such coating method can employ suitable in-situ instrumentation to control the quality of the coating formed.

The deposition approach in accordance with the present invention is different from thermal spray technology currently in used in many ways such as: (a) the feed in conventional methods is a solid micron sized powder in thermal spray processes, whereas in this invention the feed is a fluid precursor; and (b) the conventional thermal spray process is considered to yield a powder with molten surface which then sticks to the substrate, whereas in this invention, as the hot vapor cools it is anticipated to yield a molten droplet or soft particulate that forms the coating. The advantage of forming a coating or film according to this invention is the fine to nanoscale microstructure of the resultant coating or film.

Furthermore, it is contemplated that the present invention will yield additional benefits in the ability to easily transport fluids within the process, the ability to form coatings, and the ability to form wide range of compositions (oxides, carbides, nitrides, borides, multimetal compositions, composites, etc.) from a limited collection of precursors through mixing and other methods as taught herein.

A coating, film, or component may also be prepared by dispersing the dispersed nanopowder, followed by applying various known methods such as, but not limited to, electrophoretic deposition, magnetophoretic deposition, spin coating, dip coating, spraying, brushing, screen printing, ink-jet printing, toner printing, and sintering. The nanopowders may be thermally treated or reacted to enhance their electrical, optical, photonic, catalytic, thermal, magnetic, structural, electronic, emission, processing, or forming properties before such a step.

The powder may be post-processed to further improve its performance or characteristics such as flowability. For example, the post-processing of the dispersed powder may be include one or more of the following steps in any order: air classification, sieving, drying, reduction, chemical reaction with liquid, chemical reaction with gases, humidification, surface treatment, coating, pyrolysis, combustion, casting, dispersion, dissolution, suspension, molding, hipping, pressing, milling, composite forming, coarsening, mixing, agglomeration, de-agglomeration, weighing, and packaging. A non-limiting illustration of such post-processing would be where the dispersed powder are dissolved in a media selected such that the carrier particle dissolves in the media while the attached particles do not dissolve in the media. This post-processing can produce hollow nanostructured or sub-micron particles. Similarly, if the dispersed particles comprise of a polymeric carrier powders and the attached particles are ceramic, pyrolysis or combustion can also be utilized to make hollow particles. Such hollow particles are anticipated to have unusual properties such as lower effective density, low effective dielectric constant, lower effective thermal conductivity.

Uses

Dispersed powders have numerous applications in industries such as, but not limited to, catalysis, biomedical, pharmaceuticals, sensor, electronic, telecom, optics, electrical, photonic, thermal, piezo, magnetic and electrochemical products.

Biomedical implants and surgical tools can benefit from dispersed powders. It is expected that nano-dispersed powders can enable implants with modulus and other properties that match the part being replaced. The match is expected to be within 10% of the target properties. The surgical tools produced using nano-dispersed powders are expected to offer strength that is at least 10% higher than that achieved using powders without nano-dispersion.

Powdered marker, drug carriers and inhalation particulates that reduce side effects can benefit from nano-dispersed powders. For inhalation product applications, carrier particles with a size range of 500 nm to 50 microns are preferred, and carrier particles with a geometric diameter of 1–50 μm and an aerodynamic diameter of 1–10 μm are most preferred. The nanoscale dispersed particle can be a drug or a carrier of the drug. The carrier particle can be engineered to favor prolonged release. For injectable product applications, carrier particles with a size range of 100 nm to 25 microns are preferred, and carrier particles with a geometric diameter of 0.1–5 μm and an aerodynamic diameter of 0.1–1 μm are most preferred. The nanoscale dispersed particles can be markers, tracers, drug vehicles or target carriers.

Another category of application of nano-dispersed powders is phosphors. Phosphors emit light when exposed to radiation. Not-limiting illustrations of phosphors include $Zn_2SiO_4$:Mn, ZnS:Ag, ZnO:Zn, $CaSiO_3$:Mn, $Y_3Al_5O_{12}$:Ce, $Y_2O_3$:Eu, $Y_2SiO_5$:Ce, $Y_3(Al,Ga)_5O_{12}$:Tb, $BaO.6Al_2O_3$:Mn, $BaMg_2Al_{16}O_{27}$:Eu, CsI:Na, and CaS:Ce,Sm. It is expected that the methods of manufacture and other teachings of this invention can be applied wherein the major phase of the phosphor is the carrier particle and the minor phase is the nano-dispersed particle. As a non-limiting example, for $Y_3Al_5O_{12}$:Ce, $Y_3Al_5O_{12}$ can be the carrier particle while Ce is the nano-dispersed phase on the surface of the carrier. For phosphor product applications, carrier particles with a size range of 50 nm to 25 microns are preferred, and carrier particles with a geometric diameter of 0.5–10 microns are preferred. The dispersed particles with a size range of 1 nm to 0.5 microns are preferred, and dispersed particles with a geometric diameter of 1–100 nanometers are preferred. It is anticipated that the light emitting efficiency of nano-dispersed phosphor powders will be higher by 5% or more than phosphor powder of equivalent composition that is not dispersed. The scope of this invention includes Stoke and anti-Stoke phosphors. Nano-dispersed phosphor powders can be used in lamps, cathode ray tubes, field emission displays, plasma display panels, scintillators, X-ray detectors, IR detectors, UV detectors and laser detectors. Nano-dispersed phosphor powders can also be used in printing inks, or dispersed in plastics to prevent forgery and counterfeiting of currency, original works of art, passports, credit cards, bank checks, and other documents or products. The nano-dispersed powders can also be used to prepare optical networking components such as detectors, emitters, photodiodes, and phototransistors.

Another broad use of nano-dispersed powders is in electrical and electronic components such as capacitors, inductors, resistors, thermistors, sensors and varistors. Nano-dispersed particles can increase the reliability of these components by 10% or more when used as electroceramic dopants. Furthermore, nano-dispersed particles can enable miniaturization of these components by enabling ceramic layer thicknesses below 500 nm and electrode layer thicknesses below 400 nm.

Electrochemical capacitors prepared from nano-dispersed powders are expected to have charge densities that are 10% higher than those prepared from non-dispersed powders of equivalent composition. The electrochemical capacitors are also expected to offer high volumetric efficiencies, and longer mean times between failures. Batteries prepared from nano-dispersed powders can offer power densities that are 5% higher than those prepared from non-dispersed powders of equivalent composition. Chemical sensors prepared from nano-dispersed powder are expected to offer sensitivities that are at least 10% higher than those prepared from non-dispersed powders of equivalent composition.

A major application area for nano-dispersed powders produced using the high temperature process of this invention is in chemical catalysis. Catalytic materials that are prepared from nano-dispersed powders are expected to last 10% or more longer and give superior yields and selectivity than catalytic materials prepared from non-dispersed powders of equivalent composition. They are also expected to offer turn over rates that are 5% higher than those prepared from non-dispersed powders of equivalent composition. For this application, the process of this invention for producing nano-dispersed powders can additionally offer desirable porosity, structural strength, and uniformity. Examples of such applications include (a) catalytic transformation of less valuable chemicals and material feed stocks into more valuable chemicals and materials and (b) catalytic transformation of more hazardous chemicals and materials into less hazardous or non-hazardous forms of substances.

Other applications of nano-dispersed powders include (a) fillers for polymers, ceramics, and metal matrix composites and (b) dopants for electronic, magnetic, thermal, piezo, electrical, tooling, structural, inks, paints, and topical health products.

Magnetic devices prepared from dispersed powders are expected to offer superior magnetic performance. In general, nano-dispersed powders offer a means of improving the value-added performance of existing products that are produced from non-dispersed powders.

In some applications where material cost is a critical parameter, affordability can be achieved by combining low cost carrier powders with highly functional but somewhat more expensive attached nanoparticles thereby yielding more affordable yet high performance nano-dispersed powders on a per unit weight basis. As an added benefit, improved ability to process micron size carrier powders can accelerate the adoption of nano-dispersed powders in commerce.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A phosphor composition comprising dispersed powder comprising:
   a sub-micron carrier particle having a first composition; and
   nanoscale particles of a second composition that are dispersed on and attached to the surface of the carrier particle in a mechanically stable state, wherein the attached particles are smaller than the carrier particle and wherein at least two neighboring attached particles on the surface of said carrier particle do not touch each other at 300 Kelvin.

2. The composition of matter of claim 1, wherein the distance between the at least two neighboring attached particles on the surface of the carrier that do not touch each other is at least 2 Angstroms.

3. The composition of matter of claim 1, wherein said distance is greater than 5 Angstroms.

4. The composition of matter of claim 1, wherein said distance is greater than 10 Angstroms.

5. The composition of matter of claim 1, wherein said distance is greater than 50 Angstroms.

6. The composition of matter of claim 1, wherein the ratio of the average diameter of the carrier particles and the average diameter of the attached particles is greater than or equal to 2.

7. The composition of matter of claim 1, wherein said ratio is greater than 10.

8. The composition of matter of claim 1, wherein the surfaces of the attached particle and carrier particle interact physically, chemically, electrochemically.

9. The composition of matter of claim 1, wherein the carrier particle comprise nanoscale particle.

10. The composition of matter of claim 1, wherein the composition of the attached particle is selected from the group consisting of rare earths, metals, and alloys.

11. The composition of matter of claim 1, wherein the attached particle comprises a multi-metal composition.

12. The composition of matter of claim 1, wherein a composition of the carrier particle is selected from the group consisting of oxides, sulfides, aluminate, silicate, halide and rare earth comprising compositions.

13. The composition of matter of claim 1, wherein the phosphor comprises a Stoke phosphor.

14. The composition of matter of claim 1, wherein the phosphor comprises an anti-Stoke phosphor.

15. A product containing the composition of matter of claim 1.

16. The composition of matter of claim 1, wherein the carrier particles have an aspect ratio greater than 1.

17. A phosphor comprising dispersed powder comprising:
    a carrier particle having a first composition;
    nanoscale particles of a second composition that are dispersed on and attached to a surface of the carrier particle in a mechanically stable state, wherein the attached particles are smaller than the carrier particle and wherein at least two neighboring attached particles on the surface of said carrier particle do not touch each other at 300 Kelvin;
    wherein the carrier particles have a size less than 25 microns;
    wherein the dispersed particles have a size less than 100 nanometers;
    wherein the first composition is selected from the group consisting of oxides, chalcogenides, borides, carbide, nitrides, metals, alloys and polymers,
    wherein the second composition is a phosphor powder; and
    wherein the dispersed powder prepared from the carrier particles and the dispersed particles exhibits a light emitting efficiency that is higher by at least 5% than the phosphor powder that is not dispersed.

18. A product containing the phosphor of claim 17.

* * * * *